| United States Patent [19] | [11] 4,177,787 |
|---|---|
| Hattori et al. | [45] Dec. 11, 1979 |

[54] DETERIORATED CONDITION DETECTING APPARATUS FOR AN OXYGEN SENSOR

[75] Inventors: Tadashi Hattori, Okazaki; Hiroaki Yamaguchi, Aichi; Takamichi Nakase, Gamagori, all of Japan

[73] Assignee: Nippon Soken, Inc., Nishio, Japan

[21] Appl. No.: 815,832

[22] Filed: Jul. 14, 1977

[30] Foreign Application Priority Data

Aug. 8, 1976 [JP] Japan .................................. 51-94120

[51] Int. Cl.² .......................... F02B 75/10; F02B 77/08
[52] U.S. Cl. ............................ 123/198 D; 123/32 EE; 123/119 EC; 60/277
[58] Field of Search ....... 123/198 D, 119 EC, 32 EE, 123/32 EA; 60/276, 277; 73/118

[56] References Cited

U.S. PATENT DOCUMENTS

| 3,962,866 | 6/1976 | Neidhard et al. ...................... 60/276 |
|---|---|---|
| 3,969,932 | 7/1976 | Rieger et al. ........................... 73/118 |
| 4,007,589 | 2/1977 | Neidhard et al. ...................... 60/276 |
| 4,088,096 | 5/1978 | Bossi et al. ......................... 60/276 Y |

FOREIGN PATENT DOCUMENTS 2526926  1/1976  Fed. Rep. of Germany ............. 60/276

Primary Examiner—Ira S. Lazarus
Attorney, Agent, or Firm—Cushman, Darby & Cushman

[57] ABSTRACT

An apparatus for detecting a deteriorated condition of an oxygen concentration sensor mounted in an exhaust pipe for an internal combustion engine for controlling an air-fuel ratio is described. The apparatus includes, in addition to the sensor, a reference oxygen concentration sensor mounted in the exhaust pipe downstream of a cleaning device, and a discrimination unit for determining the deterioration of the oxygen concentration sensor for controlling the air-fuel ratio by measuring at least one of a duty factor and a period of an output signal from the reference oxygen concentration sensor.

6 Claims, 12 Drawing Figures

4,177,787

DETERIORATED CONDITION DETECTING APPARATUS FOR AN OXYGEN SENSOR

FIELD OF THE INVENTION

The present invention relates to a deteriorated condition detecting apparatus for an oxygen concentration sensor, and more particularly to a deteriorated condition detecting apparatus for an oxygen concentration sensor used in the feedback control of air-fuel ratio in an internal combustion engine.

DESCRIPTION OF THE PRIOR ART

Figure 1:
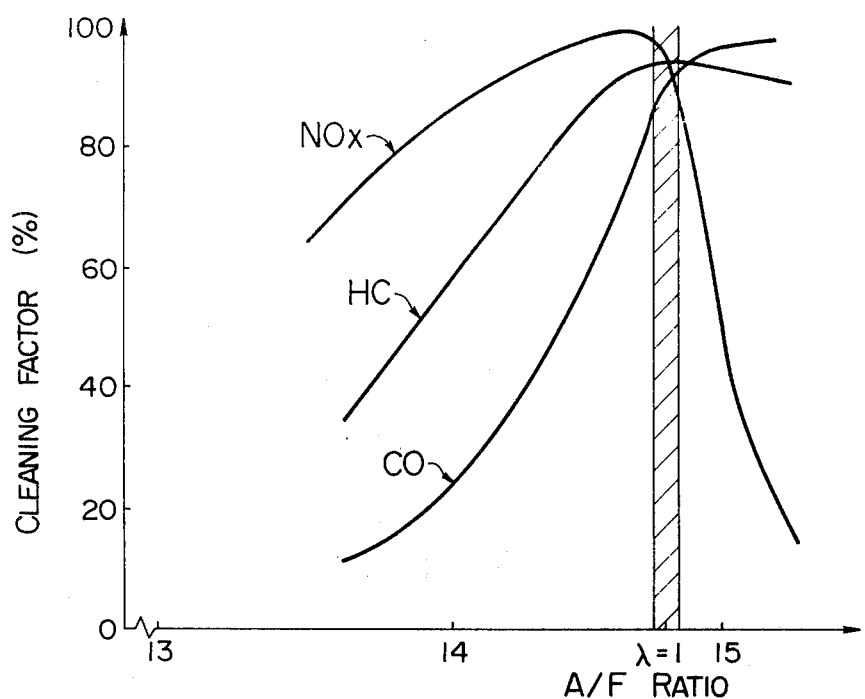
FIG. 1 shows characteristic curves illustrating a cleaning factor relative to an air-fuel ratio of a ternary catalyst used for cleaning exhaust gas of an internal combustion engine.

It has been known to use a ternary catalyst to clean exhaust gas (particularly CO, HC, NOx) exhausted from an internal combustion engine of a motor vehicle. The ternary catalyst exhibits high cleaning factors to the respective noxious components CO, HC and NOx when an air-fuel ratio of air-fuel mixture is near stoichiometric air-fuel ratio (air transmittion rate $\lambda=1$) shown by hatched area in FIG. 1. Accordingly, when the ternary catalyst is used to clean the exhaust gas of the internal combustion engine, it is necessary to accurately control the air-fuel ratio of the air-fuel mixture to the stoichiometric air-fuel ratio in a suction system or an exhaust system of the internal combustion engine. As an approach to meet the above requirement, it has been proposed to feedback control the air-fuel ratio.

In this air-fuel ratio control, an oxygen concentration sensor (hereinafter simply referred to $O_2$ sensor) consisting of oxygen ion conductive metal oxide such as zirconium dioxide is used. As shown by a characteristic curve A shown in FIG. 2, this type of $O_2$ sensor senses the presence of oxygen in the exhaust gas to produce a low level voltage when the air-fuel ratio of the air-fuel mixture is higher than the stoichiometric air-fuel ratio and the output voltage level of the sensor is reversed substantially stepwise around the stoichiometric air-fuel ratio ($\lambda=1$). However, since the $O_2$ sensor is mounted in the exhaust gas environment, the output characteristic thereof is deteriorated by the deposition of noxious material such as lead (Pb) in the exhaust gas. The deterioration of the output characteristic mainly includes (1) increase of internal resistance, (2) decrease of electromotive force, and (3) increase of response time. Where the $O_2$ sensor has been deteriorated, it is not possible to attain highly accurate air-fuel ratio control by the feedback control but the air-fuel ratio obtained by the feedback control will greatly deviates from a desired air-fuel ratio resulting in deteriorated running of the internal combustion engine.

The deterioration of the output characteristic of the $O_2$ sensor is discussed below in detail.

Figure 2:
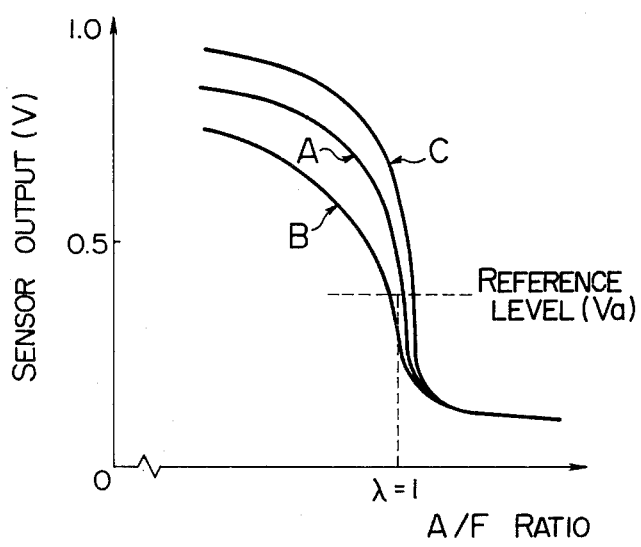
FIG. 2 shows characteristic curves illustrating outputs of an oxygen concentration sensor relative to the air-fuel ratio.
Figure 3:
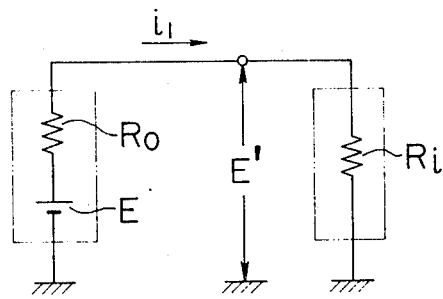
FIGS. 3 and 4 show equivalent circuit diagrams for explaining the operation of the oxygen concentration sensor.
Figure 4:
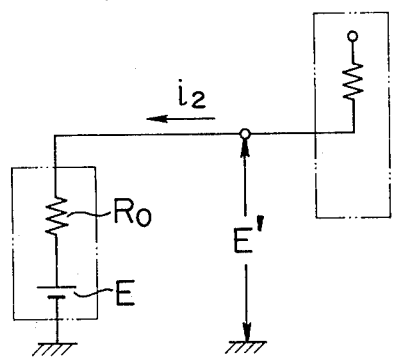

(1) Increase of the internal resistance

Where a current $i_1$ is fed into a control circuit from the $O_2$ sensor as shown in FIG. 3, an apparent output voltage $E'$ of the $O_2$ sensor is equivalently given by $E'=E \times R_i/(R_o+R_i)$, where $R_o$ is an internal resistance of the $O_2$ sensor, $E$ is an electromotive force, and $R_i$ is an input impedance of the control circuit which processes the output voltage of the $O_2$ sensor. Conversely, where a current $i_2$ is fed into the $O_2$ sensor from the control circuit as shown in FIG. 4, an apparent output voltage $E'$ of the $O_2$ sensor is equivalently given by $E'=E+R_o \times i_2$. Accordingly, when the current $i_o$ is passed out of the $O_2$ sensor, the output voltage $E'$ decreases with the increase of the internal resistance $R_o$ as shown by a characteristic curve B of FIG. 2 and the air-fuel ratio deviates to the smaller side ($\lambda<1$, RICH), whereas when the current $i_2$ is passed into the $O_2$ sensor the output voltage $E'$ increases with the increase of the internal resistance $R_o$ as shown by a characteristic curve C in FIG. 2 and the air-fuel ratio deviates to the larger side ($\lambda>1$, LEAN).

(2) Decrease of electromotive force

When the electromotive force $E$ of the $O_2$ sensor decreases, the output voltage $E'$ thereof decreases as shown by the characteristic curve B in FIG. 2 in both circuit arrangement illustrated in FIGS. 3 and 4, and the air-fuel ratio deviates to the smaller side (rich side).

(3) Increase of response time

Figure 5:
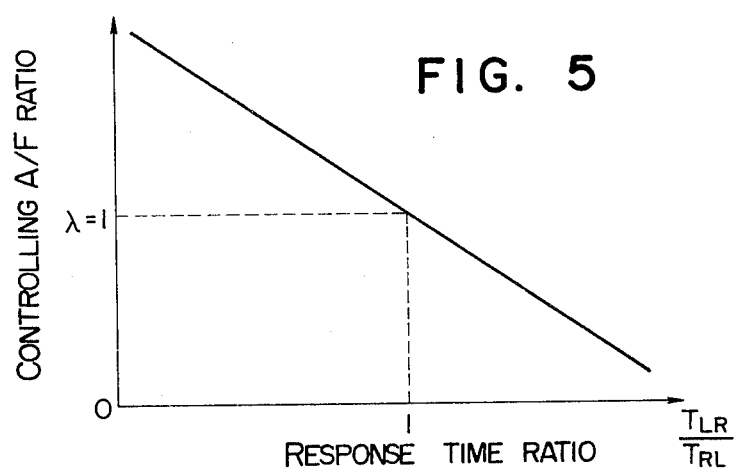
FIG. 5 shows a characteristic curve illustrating the change of air-fuel ratio relative to a response time ratio of the oxygen concentration sensor.

The increase of the response time of the $O_2$ sensor includes the increase of the response time $T_{LR}$ from the lean side (low level output voltage) to the rich side (high level output voltage) and the increase of the response time $T_{RL}$ from the rich side to the lean side. As the response time $T_{LR}$ increase, the air-fuel ratio deviates toward the rich (R) side, and as the response time $T_{RL}$ increases the air-fuel ratio deviates toward the lean (L) side. As shown in FIG. 5, as a ratio of the response time $T_{LR}$ to the response time $T_{RL}$ ($T_{LR}/T_{RL}$) increases, the air-fuel ratio deviates toward the rich side. Furthermore, when both the response times $T_{LR}$ and $T_{RL}$ increase, the range of variation of the air-fuel ratio increases and the air-fuel ratio deviates beyond the stoichiometric air-fuel ratio region shown by hatching in FIG. 1, which is a high cleaning factor region.

Figure 6:
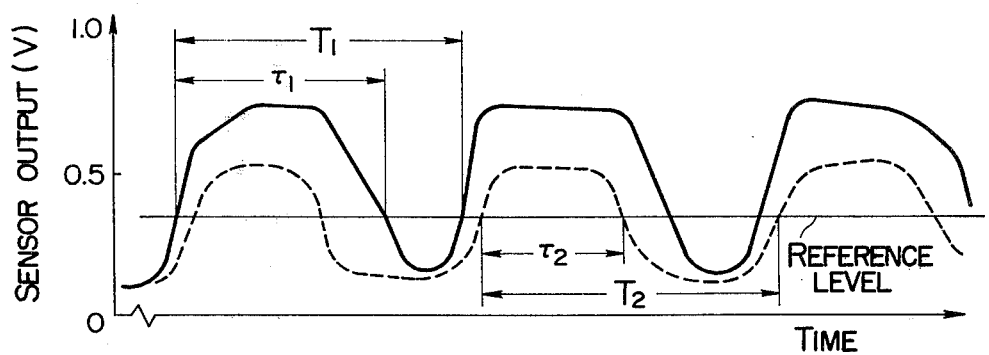
FIG. 6 shows signal waveforms illustrating the change of the output of the oxygen concentration sensor with time.

The deteriorated condition of the $O_2$ sensor can be determined from the above three factors. In this case, the deteriorated condition can be determined by the output voltage waveform of the $O_2$ sensor. That is, the output waveform of a normal $O_2$ sensor has a duty factor $d_2$ of $\tau_2/T_2$ as shown by a broken line in FIG. 6, whereas the output waveform of an $O_2$ sensor which tends to cause the controlling air-fuel ratio to be deviated toward the lean side has a duty factor $d_1$ of $\tau_1/T_1$. If $T_1=T_2$, then the duty factor $d_1$ is larger than $d_2$ ($d_1>d_2$). Conversely, the output waveform of an $O_2$ sensor which tends to cause the controlling air-fuel ratio to be deviated to the rich side has the duty factor $d_1$ which is smaller than $d_2$ if $T_1=T_2$. In this manner, the relation of the output voltage of the $O_2$ sensor and the duty factor is such that the duty factor increases as the output voltage increases. Accordingly, the deteriorated condition of the $O_2$ sensor can be determined by measuring the duty factor d of the output waveform of the $O_2$ sensor. If the response of the $O_2$ sensor is deteriorated as a whole, a period T of the output waveform becomes longer. Accordingly, the deteriorated condition of the $O_2$ sensor may also be determined by measuring the period T.

SUMMARY OF THE INVENTION

The present invention is made based on the discussion of the above matters and it is an object of the present invention to provide a deteriorated condition detecting apparatus which can determine the deteriorated condition of an $O_2$ sensor being tested for deteriorated condition by maintaining the $O_2$ sensor under test in an air-fuel ratio controlling operation and comparing the result of control thereby with an output waveform of a reference $O_2$ sensor which is not deteriorated.

DESCRIPTION OF THE PREFERRED EMBODIMENT

Figure 7:
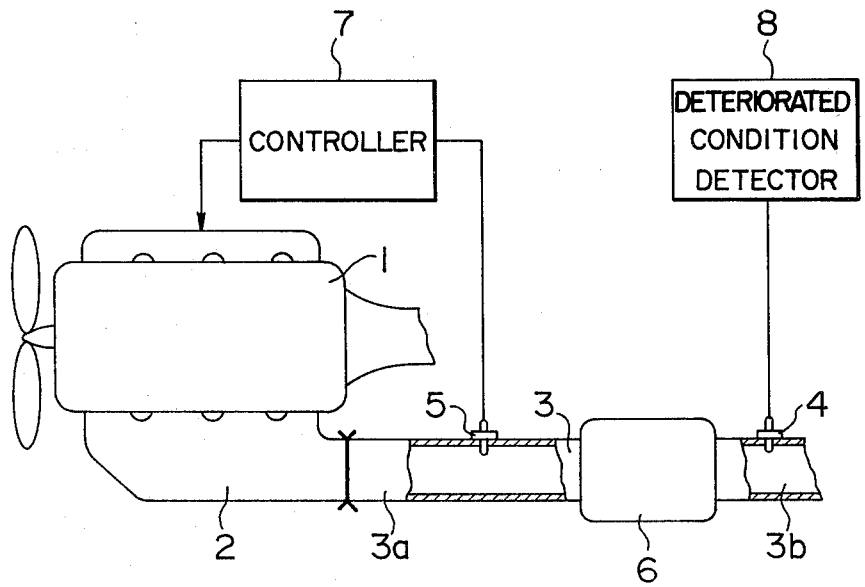
FIG. 7 is a schematic diagram illustrating one embodiment of the present invention.

The present invention is now explained in conjunction with the preferred embodiments thereof shown in FIGS. 7 through 12. FIG. 7 shows an embodiment which uses an $O_2$ sensor to control the air-fuel ratio control of an internal combustion engine. In FIG. 7, numeral 1 denotes the internal combustion engine, 2 an exhaust manifold, 3 an exhaust pipe, 3a and 3b are inlet exhaust passage and outlet exhaust passage for a ternary catalytic converter 6, 4 a reference $O_2$ sensor which is not deteriorated, 5 an $O_2$ sensor under test, 7 a control unit which processes an output signal of the $O_2$ sensor 5 under test to control an air-fuel ratio of an air-fuel mixture in a suction system or exhaust system, and 8 a deteriorated condition discrimination unit for discriminating the deteriorated condition of the $O_2$ sensor 5 under test by an output signal of the reference $O_2$ sensor 4. In FIG. 7, a feedback control system using the $O_2$ sensor 5 under test is of known type, and if the $O_2$ sensor 5 has been deteriorated, the exhaust gas from the catalytic converter 6 shows the result of control which reflects the deterioration. Thus, by mounting the reference $O_2$ sensor at the outlet of the catalytic converter 6 and discriminating the control result of the air-fuel ratio obtained by the $O_2$ sensor 5 under test, the deteriorated condition of the $O_2$ sensor 5 can be determined. Since the exhaust gas from the internal combustion engine 1 is cleaned by the catalytic converter 6, the reference $O_2$ sensor 4 is rarely deteriorated by the exhaust gas.

Figure 8:
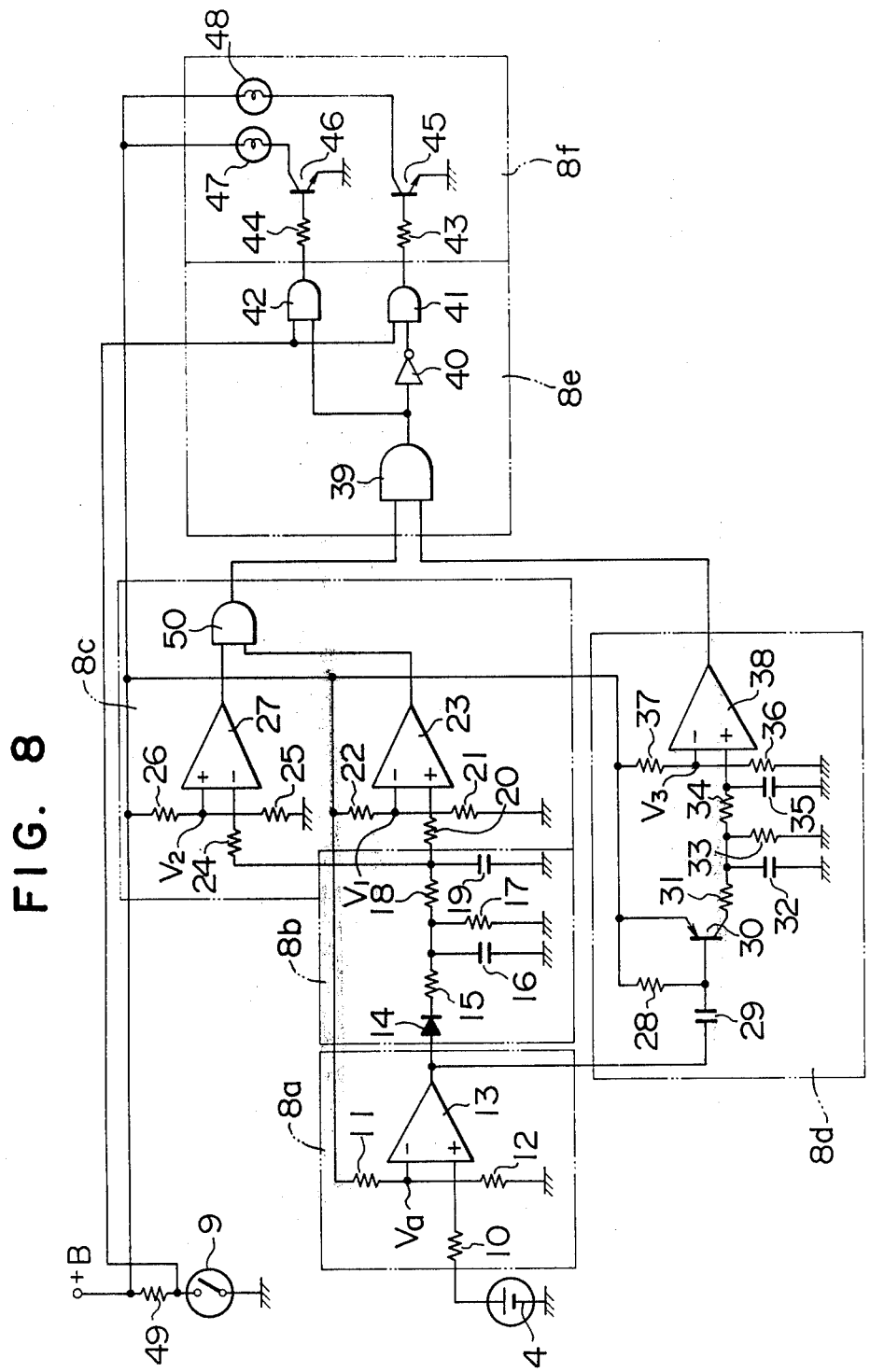
FIG. 8 is an electrical circuit diagram illustrating the detail of a deteriorated condition discriminating unit shown in FIG. 7.
Figure 9:
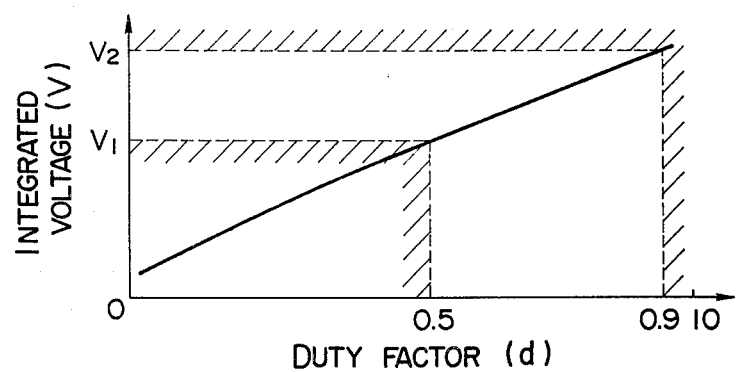
FIG. 9 shows a characteristic curve of duty factor vs integrated voltage for explaining the operation of an integration circuit shown in FIG. 8.

FIG. 8 shows the details of the reference $O_2$ sensor 4 and the deteriorated condition discrimination unit 8. They are explained in detail. An air-fuel ratio discrimination circuit 8a comprises resistors 10, 11 and 12, and a comparator 13, and it produces "1" or "0" voltage depending on the comparison result of the output voltage of the reference $O_2$ sensor 4 and a reference voltage $V_a$ corresponding to the stoichiometric air-fuel ratio. Namely, the discrimination circuit 3a produces "1" output when the air-fuel ratio is on the rich side (no oxygen exists in the exhaust gas) while it produces "0" output when the air-fuel ratio is on the lean side (oxygen exists in the exhaust gas).

An integration circuit 8b comprises a diode 14, resistors 15, 17 and 18 and capacitors 16 and 19, and it integrates the "1" voltage from the air-fuel ratio discrimination circuit 8a during the duration thereof to produce a voltage which is proportional to the integration period, that is, a duty factor d.

A duty factor discrimination circuit 8c comprises a first comparator circuit including resistors 20, 21 and 22 and a comparator 23, a second comparator circuit including resistors 24, 25 and 26 and a comparator 27, and an AND gate 50, and it discriminates the duty factor d based on the integrated output voltage from the integration circuit 8b. By properly setting a voltage $V_1$ divided by the resistors 21 and 22, the first comparator circuit produces "0" voltage when the duty factor d ($\tau/T$) is smaller than 0.5 while it produces "1" voltage when the duty factor d is larger than 0.5. By properly setting a voltage $V_2$ divided by the resistors 25 and 26, the second comparator circuit produces "1" voltage when the duty factor d is smaller than 0.9 while it produces "0" voltage when the duty factor is larger than 0.9. Accordingly, the output of the AND gate 50 is at "1" level when the duty factor d meets the relation $0.5<d<0.9$ and at "0" level when the duty factor is beyond the above range.

Thus, if the duty factor d meets the relation $0.5<d<0.9$, it is determined that the air-fuel ratio control by the $O_2$ sensor is being performed satisfactorily and the $O_2$ sensor 5 is not deteriorated. When the duty factor d is smaller than 0.5 (d<0.5), it is determined that the air-fuel mixture is too lean, and when the duty factor d is larger than 0.9 it is determined that the air-fuel mixture is too rich. In any cases, it is determined that the $O_2$ sensor 5 under test has been deteriorated. It should be understood that the duty factor d is set in accordance with a particular specification of the internal combustion engine.

A period discrimination circuit 8d produces a differentiated pulse by a resistor 28, a capacitor 29 and a transistor 30 when the output of the air-fuel ratio discrimination circuit 8a changes from "1" voltage to "0" voltage and integrates the differentiated pulse by an integration circuit including resistors 31, 33 and 34 and capacitors 32 and 35 to convert the output of the air-fuel ratio discrimination circuit 8a, that is, the output period T of the $O_2$ sensor 4 to an analog voltage. Accordingly, as the period T becomes shorter, the integrated value increases and as the period T becomes longer the integrated value decreases. The period discrimination circuit 8d further compares the integrated output with a reference voltage $V_3$ by a comparator circuit comprising resistors 36 and 37 and a comparator 38 to produce "0" voltage when the period T is longer than the period defined by the voltage $V_3$ and produce "1" voltage when the period T is shorter.

Logical determination circuit 8e comprises AND gates 39, 41 and 42 and a NOT gate 40, the AND gates 41 and 42 being connected to a condition detecting switch 9, which is designed to produce "1" voltage when it is ready for the discrimination of the deteriorated condition of the O₂ sensor 5. It may be responsive to the rotational speed of the engine, exhaust gas temperature or suction pipe pressure. The condition detecting switch 9 is provided because the control of the air-fuel ratio to a ratio other than the stoichiometric air-fuel ratio may be required in the feedback control of the air-fuel ratio. The AND gate 42 produces "1" voltage only when both the duty factor discrimination circuit 8c and the period discrimination circuit 8d produce "1" voltages indicating that the O₂ sensor 5 is not deteriorated and the condition detecting switch 9 produces "1" voltage. On the other hand, the AND gate 41 produces "1" voltage only when at least one of the duty factor discrimination circuit 8a and the period discrimination circuit 8d produces "0" voltage indicating the deteriorated condition of the O₂ sensor 5 and the condition detecting switch 9 produces "1" output.

An alarm circuit 8f comprises resistors 43 and 44, transistors 45 and 46 and lamps 47 and 48. When the transistor 45 is applied with "1" voltage for conduction, the lamp 48 is lit, and when the transistor 46 is applied with "1" voltage for conduction, the lamp 47 is lit. Accordingly, when the logical determination circuit 8e determines the deteriorated condition of the O₂ sensor 5, the lamp 48 is lit, and when the circuit 8e determines that the O₂ sensor 5 is not deteriorated, the lamp 47 is lit.

Figure 10:
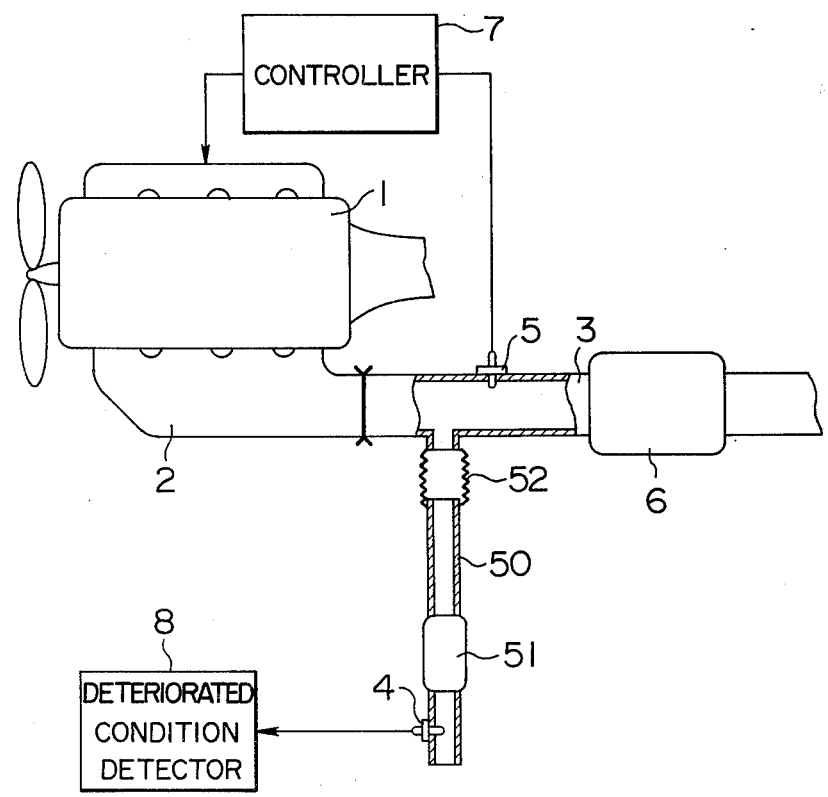
FIG. 10 is a schematic diagram illustrating another embodiment of the present invention.

While the reference O₂ sensor 4 is mounted at the outlet of the catalytic converter 6 in the above embodiment, the reference O₂ sensor 4 and the catalytic converter 51 may be connected to the exhaust pipe 3 through a sampling tube 50 and a connecting tube 52, as shown in FIG. 10.

Figure 11:
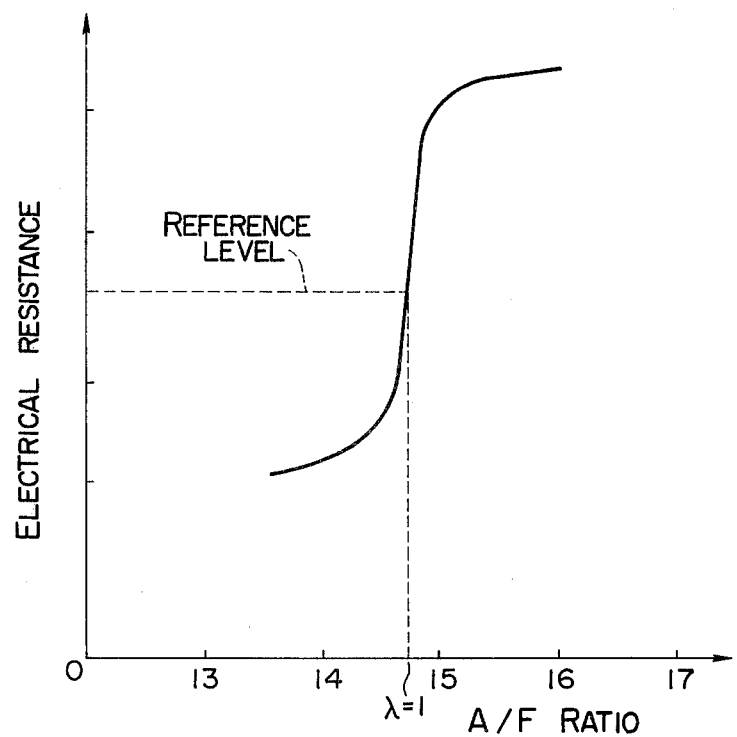
FIG. 11 shows a characteristic curve illustrating the change of electrical resistance, relative to the air-fuel ratio, of an oxygen concentration sensor using a transitional metal oxide.
Figure 12:
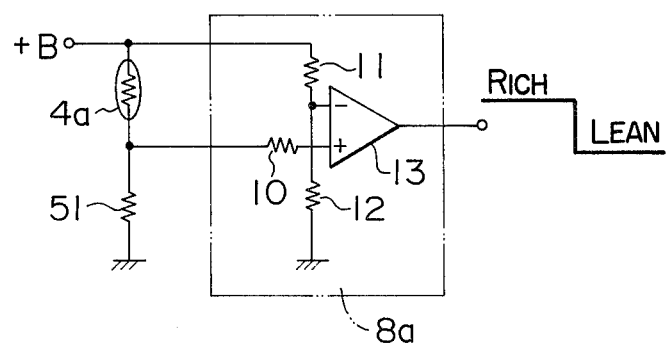
FIG. 12 shows an electrical circuit diagram suited for the detection of the deteriorated condition of the oxygen concentration sensor shown in FIG. 11.

While the above embodiment is related to the O₂ sensor using oxygen ion conductive metal oxide such as zirconium dioxide, a sensor using a transitional metal oxide such as titanium dioxide an electrical resistance of which varies with gas composition of the exhaust gas may be used, as shown in FIG. 11, to detect the deteriorated condition in a similar manner. In this case, since the electrical resistance represents the electrical characteristic of the sensor, a resistor 51 is connected to a sensor 4a and a voltage divided thereby is applied to the air-fuel ratio discrimination circuit 8a, as shown in FIG. 12.

As described hereinabove, according to the present invention, the reference oxygen concentration sensor is provided in addition to the oxygen concentration sensor used for the feedback control of the air-fuel ratio and at least one of the duty factor and the period of the output signal produced by the reference oxygen concentration sensor under the feedback control of the air-fuel ratio is measured to determine the deteriorated condition of the oxygen concentration sensor used for the feedback control. Accordingly, the deteriorated condition can be readily determined without paying attention to the analysis result of the exhaust gas and the specification of the internal combustion engine.

We claim:
1. In combination with an engine control system having a catalytic converter mounted in an exhaust passage of the engine, an oxygen sensor mounted upstream of said converter for generating an output signal the signal level of which changes when oxygen concentration present upstream of said converter in said exhaust passage changes across a value corresponding to a stoichiometric ratio of air-fuel mixture supplied to said engine, and a controller connected to said oxygen sensor for feeding back said output signal thereby controlling the oxygen concentration in said exhaust passage towards said value, a sensor deteriorated condition detecting apparatus comprising:
a reference oxygen sensor mounted in said exhaust passage downstream of said catalytic converter and adapted to be correctly responsive to the oxygen concentration present downstream of said converter in said exhaust passage for generating a reference output signal in the same manner as said oxygen sensor connected to said controller;
first comparing means connected to said reference oxygen sensor for generating a first comparison signal which alternately changes between predetermined constant high and low levels in response to changes of said reference output signal;
first integrating means connected to said first comparing means for generating a first integration signal which changes proportionally to the duty factor of said first comparison signal;
second comparing means connected to said first integrating means for generating a second comparison signal when said first integration signal becomes higher and lower than predetermined upper and lower limits respectively; and
warning means connected to said second comparing means for warning at least of the deteriorated condition of said oxygen sensor connected to said controller in response to said second comparison signal.

2. A sensor deteriorated condition detecting apparatus according to claim 1 further comprising:
second integrating means connected to said first comparing means for generating a second integration signal which changes as the cycle period of said first comparison signal changes;
third comparing means connected to said second integrating means for generating a third comparison signal when said second integration signal reaches a predetermined limit; and
logic actuating means connected to said second and third comparing means for actuating said warning means when at least one of said second and third comparison signals are generated.

3. A sensor deteriorated condition detecting apparatus according to claim 1, wherein said second comparing means includes two comparators, one and the other thereof being adapted to compare said first integration signal with said predetermined upper and lower limits respectively.

4. A sensor deteriorated condition detecting apparatus according to claim 1, wherein said warning means includes a first and a second warners adapted to be actuated in response to the presence and the absence of said second comparison signal respectively.

5. A sensor deteriorated condition detecting apparatus according to claim 2, wherein said second comparing means includes two comparator, one and the other thereof being adapted to compare said first integration signal with said predetermined upper and lower limits respectively.

6. A sensor deteriorated condition detecting apparatus according to claim 1, which further comprises a sampling pipe, connected to said exhaust passage, for introducing part of said exhaust gas to pass therethrough, and wherein said sampling pipe has a catalytic converter provided in a passage of said sampling pipe for purifying the exhaust gas passing therethrough, and said reference oxygen sensor is mounted on said sampling pipe downstream of said catalytic converter, in place of said exhaust passage.

* * * * *